(12) United States Patent
Andrade

(10) Patent No.: US 6,240,917 B1
(45) Date of Patent: Jun. 5, 2001

(54) AEROSOL HOLDING CHAMBER FOR A METERED-DOSE INHALER

(76) Inventor: Joseph R. Andrade, 131 Fox Meadow Rd., Scarsdale, NY (US) 10583

( * ) Notice: Subject to any disclaimer, the term of this patent is extended or adjusted under 35 U.S.C. 154(b) by 0 days.

(21) Appl. No.: 09/468,381

(22) Filed: Dec. 20, 1999

(51) Int. Cl.[7] ................................................. A61M 11/00
(52) U.S. Cl. ............................... 128/200.23; 128/200.22; 128/200.14
(58) Field of Search ....................... 128/200.12, 200.23, 128/200.22, 203.12

(56) References Cited

U.S. PATENT DOCUMENTS

| | | | |
|---|---|---|---|
| 4,809,692 | * | 3/1989 | Nowacki et al. ............... 128/206.24 |
| 5,012,804 | * | 5/1991 | Foley et al. ..................... 128/200.23 |
| 5,040,527 | * | 8/1991 | Larson et al. ................... 128/200.23 |
| 5,042,467 | * | 8/1991 | Foley .............................. 128/200.23 |
| 5,848,588 | * | 12/1998 | Foley et al. ..................... 128/200.23 |
| 6,026,807 | * | 2/2000 | Puderbaugh et al. ........... 128/200.23 |
| 6,039,042 | * | 3/2000 | Sladek ............................. 128/200.23 |

* cited by examiner

Primary Examiner—Glenn K. Dawson
Assistant Examiner—Darwin P. Erezo
(74) Attorney, Agent, or Firm—Herbert Dubno; Andrew Wilford

(57) ABSTRACT

An aerosol holding chamber for use with a metered-dose inhaler having a tubular outlet has an elongated body having a rear end wall formed with a hole shaped to fit snugly around the tubular outlet of the inhaler, a front end provided with a mouthpiece, and a partition defining in the body a front compartment at the mouthpiece and a rear compartment at the rear wall. A vent passage opens outward from the front compartment and a first check valve at the partition permits gas flow through the partition only from the rear compartment to the front compartment. A second check valve permits gas flow only out of the front compartment through the vent passage. An air-flow actuated noise maker in the vent passage generates an audible sound when air blown into the front compartment exits through the vent passage. The device is inserted into the user's mouth and the user first exhales into it, with the noisemaker indicating that this is happening. Once the noise stops, which indicates that the user cannot breath out any more, he or she actuates the inhaler to inject a dose into the chamber and breathes in, taking the medicament in. During the entire process the mouthpiece of the chamber remains in the user's mouth and audible feedback is provided so that it is easy to ensure that the user's lungs are as empty as possible before the drug is taken in.

5 Claims, 2 Drawing Sheets

AEROSOL HOLDING CHAMBER FOR A METERED-DOSE INHALER

FIELD OF THE INVENTION

The present invention relates to an aerosol holding chamber for a metered-dose inhaler.

BACKGROUND OF THE INVENTION

A standard metered-dose inhaler, such as sold under the trade name "FLOVENT" by GlaxoWellcome, "PROVENTIL" or "VANCERIL" by Key Pharmaceutical, or "AEROBID" by Forest Pharmaceuticals, comprises a small pressurized medication-filled cartridge and a holder formed with a short tubular mouthpiece. After shaking the device the mouthpiece is inserted into the mouth between the lips and teeth. Then the patient exhales deeply to empty his or her lungs and then takes a slow deep breath as the cartridge is actuated to release a puff of the medication that is then drawn down into the lungs, normally to apply an antiinflammatory agent to them.

Such a system is extremely effective only if used perfectly. A particular problem is that the medication must be taken deep into the lungs, so that the lungs must be as empty as possible before aspirating the medication. These devices are, however, invariably being used by those suffering from breathing difficulties who are in fact often gasping for breath when the device is being used so that getting the procedure correct is a problem, in particular for children.

This has led to the development of aids that are used with an inhaler. U.S. Pat. Nos. 5,855,202 and 5,012,804 describe such a chamber that has a rigid cylindrical compartment provided at one end with a tubular extension serving as mouthpiece and of substantially the same size and shape as the mouthpiece of the inhaler. The other end of the compartment is provided with a hole into which the mouthpiece of the inhaler is fitted and a one-way valve at this other end allows air to be drawn into the compartment. Thus, after fitting the inhaler to the compartment, the user places the mouthpiece of the holding chamber in his mouth, actuates the inhaler to shoot a puff of the medication into the compartment, and then slowly inhales to draw in the charge from the compartment. Such an arrangement can even allow the user to draw in the medication in two breaths. It is known to provide a noisemaker or whistle in the wall of the compartment so that the user can test the seal around the inhaler by sucking on the mouthpiece to see if the whistle sounds. If it does not, there is a leak.

The disadvantage of these known systems is that they still require the patient to fully empty his or her lungs before aspirating the medications. It is very difficult for many people, in particular those with breathing difficulties, to exhale deeply and then not take in any more air before using the device. Usually as the mouthpiece of the holding chamber is inserted into the user's mouth, a short breath is stolen.

OBJECTS OF THE INVENTION

It is therefore an object of the present invention to provide an improved aerosol holding chamber for a metered-dose inhaler.

Another object is the provision of such an improved aerosol holding chamber for a metered-dose inhaler which over-comes the above-given disadvantages, that is which makes it easy for the user to properly fully exhale before aspirating the medication.

SUMMARY OF THE INVENTION

An aerosol holding chamber for use with a metered-dose inhaler having a tubular outlet has according to the invention an elongated body having a rear end wall formed with a hole shaped to fit snugly around the tubular outlet of the inhaler, a front end provided with a mouthpiece, and a partition defining in the body a front compartment at the mouthpiece and a rear compartment at the rear wall. A vent passage opens outward from the front compartment and a first check valve at the partition permits gas flow through the partition only from the rear compartment to the front compartment. A second check valve permits gas flow only out of the front compartment through the vent passage. An air-flow actuated noise maker in the vent passage generates an audible sound when air blown into the front compartment exits through the vent passage.

Thus the device is inserted into the user's mouth and the user first exhales into it, with the noisemaker indicating that this is happening. Once the noise stops, which indicates that the user cannot breath out any more, he or she actuates the inhaler to inject a dose into the chamber and inhales, taking the medicament in. During the entire process the mouthpiece of the chamber remains in the user's mouth and audible feedback is provided so that it is easy to ensure that the user's lungs are as empty as possible before the drug is taken in.

The noisemaker is formed with a flow passage and has a tongue-like reed projecting into the passage. It can also be constructed as a whistle. When formed with a reed it is easy to set it up so it only vibrates with flow in one direction as a further aid for proper use.

The body has a wall formed with a through going aperture provided with another air-flow actuated noisemaker. It can operate only with outgoing air, while the first noisemaker only sounds with incoming air, and can even have a different note or sound quality from the first noisemaker.

The partition is formed with at least one through going hole. A valve disk having a flap overlying the hole in the partition forms the first check valve. The body can have an annular surface and the valve disk can have a rim engageable with the annular surface and forming the second check valve. Thus a single valve disk forms both check valves. The body is formed adjacent the surface with a plurality of inwardly open notches.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
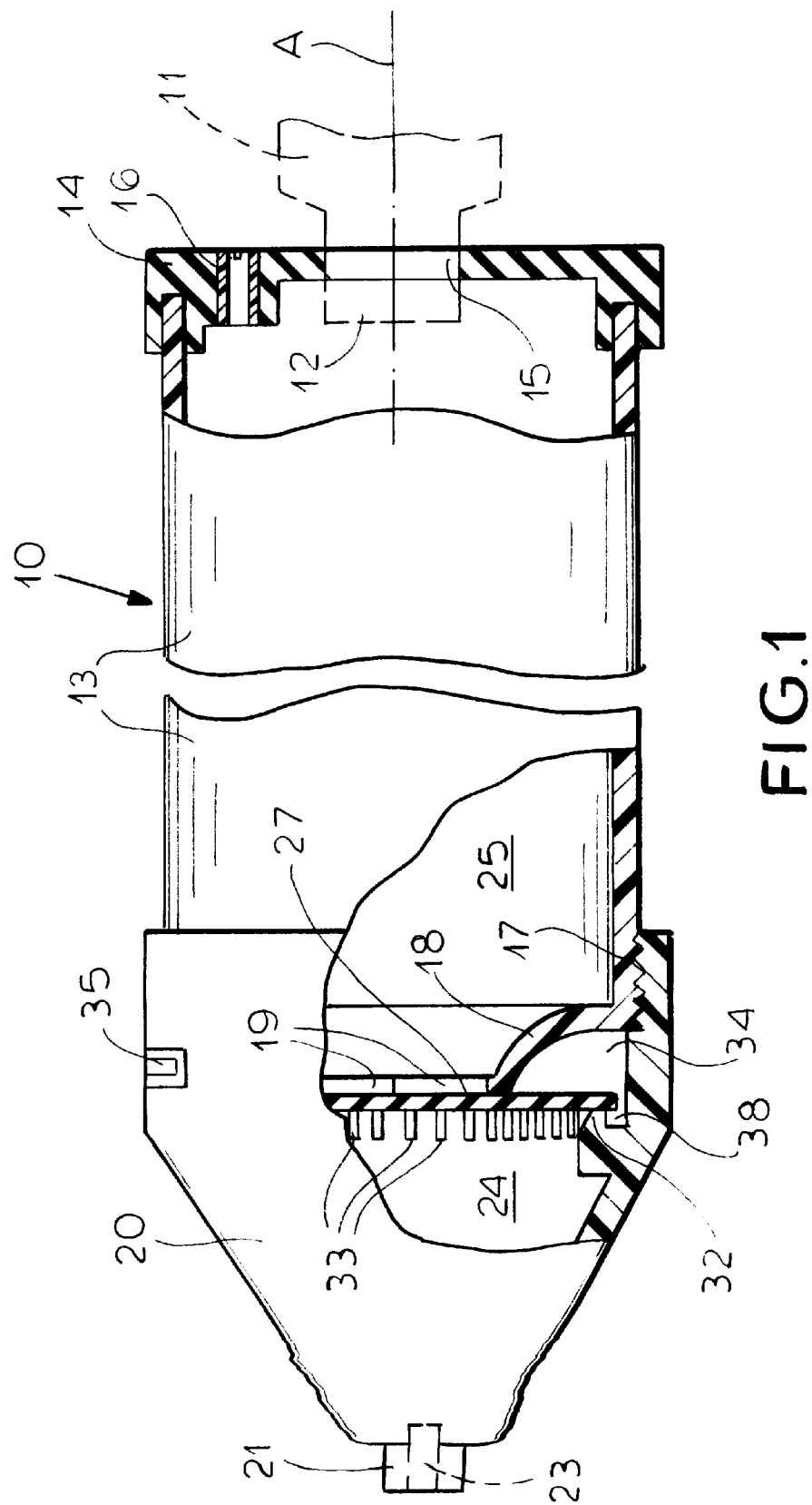
FIG. 1 is a side view partly in axial section through the system of this invention.
Figure 3:
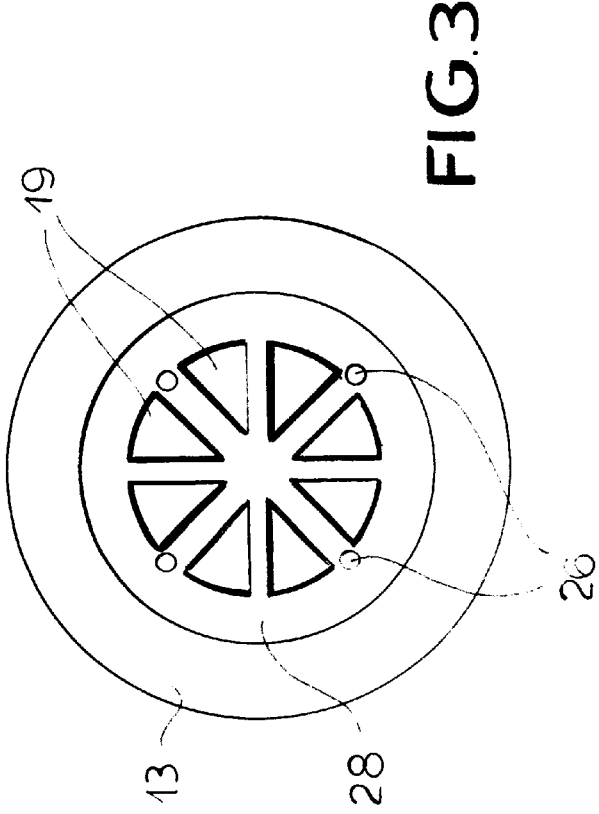
FIG. 3 is an end view of the valve seat.
Figure 2:
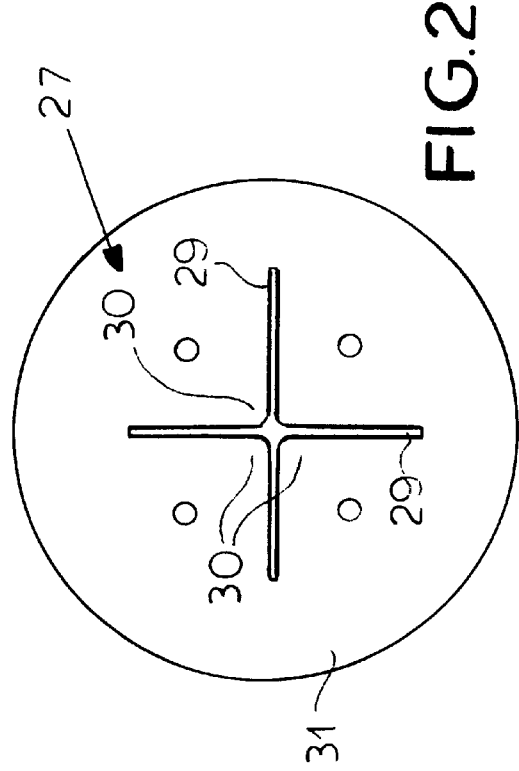
FIG. 2 is an end view of the valve member.

As seen in FIGS. 1 to 3, an aerosol holding chamber 10 according to the invention is generally centered on an axis A and is used with a metered-dose inhaler shown in dot-dash lines at 11 and having a tubular outlet 12. As is standard, actuation of the inhaler 11 will cause a metered aerosol dose of a medication to exit from the outlet tube 12.

The chamber 10 basically comprises a cylindrical body 13 centered on an axis A and provided on its rear end with a rubber cuff 14 formed centrally with a port 15 that snugly surrounds and holds the outlet tube 12. An aperture in this cuff 14, which closes the rear end of the body 13, is provided with a reed-type whistle or noisemaker 16 described below in more detail. The front end of the body 13 is formed with an external screw thread 17 and with an inwardly extending partition 18 formed with eight generally triangular through going holes 19.

A cap 20 is threaded on the screw thread 17 and is formed with a tubular mouthpiece 21 forming on the axis A a passage 23 opening into a front compartment 24 separated by the partition 18 from a rear compartment 25 formed by the body 13.

Short axially extending mounting pins 26 support an elastomeric valve disk 27 on a front face 28 of the partition 18. This disk 27 has slits 29 forming flaps 30 that normally overlie and cover the holes 19. In addition a rim 31 of the disk 27 bears axially forward on an annular array of teeth 32 of the cap 20. The cap 20 is formed inward of and between these teeth 32 with a series of inwardly and rearwardly open notches 33 normally completely covered by the rim 31 of the disk 27 and outward by a groove 28. The rear face of the disk 27 defines with the cap 20 and partition 18 a vent passage 34. Another whistle or noise-maker 35 like the device 16 is set in the wall of the cap 20 at the passage 34 so that air can only exit from the passage 34 through this noisemaker 35. There are no tooth-forming notches 33 immediately adjacent this whistle 35.

Figure 4:
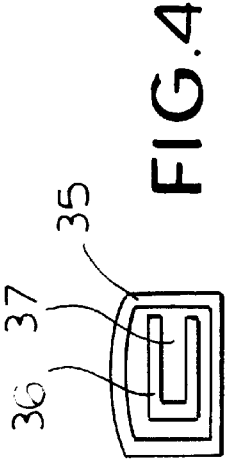
FIG. 4 is an end view of the noise maker.

As shown in FIG. 4, the noisemaker 35 is formed with a hole or port 36 into which extends a tongue-like reed 37. Air passing through the hole or port 36 under some pressure will cause the reed 37 to vibrate and generate a tone that will have a predetermined frequency.

For use the outlet tube 12 normally completely blocks the port 15. This blockage is important and can be tested by sucking air out of the device through the passage 23. Such suction will create a subatmospheric pressure in the compartment 24 that will pull the rim 31 of the membrane disk 27 tightly against the seat 32 and completely block the notches 33. Mean-while the flaps 30 will be deflected inward and air will pass through the holes 19 of the partition. If the port 15 is blocked, the only way for air to enter the compartment 25 is via the noisemaker 16 which will, therefore, emit its characteristic sound. If, however, there is substantial leakage around the outlet tube 12, the noisemaker 16 will not sound and the user will know to check the fit of the outlet tube 12 in the port 15.

Once the proper fit of the outlet tube 12 in the port 15 has been confirmed, the user then blows forcibly into the mouthpiece 21. This creates an overpressure in the front compartment 24 which will press the flaps 30 of the valve disk 27 tightly over the holes 19 and block any flow back into the rear compartment 25. The same overpressure will, however, push back the rim 31 of the disk 27 so that air can flow through the notches 33 and around the outer periphery of the disk 27 into the vent passage 34 whence it will exit the device through the noisemaker 35, which will sound.

The user is instructed therefore to first suck in on the mouthpiece 21 to confirm that the device 10 is fitted with the inhaler 11, then to blow out forcefully while listening to the noisemaker 35 until he or she cannot get anything more out.

Then, without taking the mouth off the mouthpiece, the user again inhales while operating the inhaler 11 to inject a puff of medication into the compartment 25 which is mixed with air therein and drawn through the front compartment 24 and mouthpiece 24 into the user's lungs.

The provision of two noisemakers, which have different tones, makes it extremely easy for the user to ascertain that he or she is properly using the device. The critical step of emptying the lungs, which hitherto was done by exhaling before putting the mouthpiece in the mouth, is thus carried out with the device in the mouth, eliminating any chance that a short breath is stolen before the device 10 is inserted.

Figure 5:
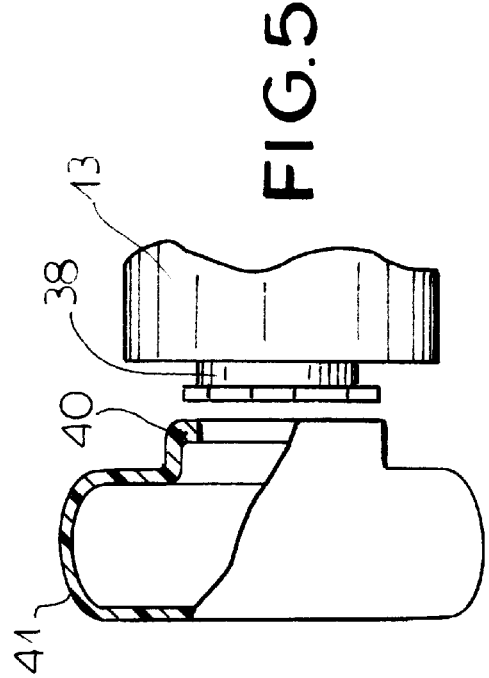
FIG. 5 is a partial view in smaller scale illustrating a variant on the system of this invention.

FIG. 5 shows how instead of the mouthpiece 21, the body 13 can have a centered annular collar 38 provided with an out-wardly directed toothed rim. A lip 40 of a flexible pediatric breathing mask 41 can be fitted over this collar 38 to allow the device to be used on small infants. The double-whistle system allows the person using it on an infant to ascertain easily if the mask is a snug fit.

I claim:

1. An aerosol holding chamber for use with a metered-dose inhaler having a tubular outlet, the holding chamber comprising:
   an elongated body having
      a wall formed with an aperture,
      a rear end wall formed with a hole shaped to fit snugly around the tubular outlet of the inhaler,
      a front end provided with a mouthpiece,
      a partition defining in the body a front compartment at the mouthpiece and a rear compartment at the rear wall, and
      a vent passage opening outward from the front compartment;
   a first check valve at the partition permitting gas flow through the partition only from the rear compartment to the front compartment;
   a second check valve permitting gas flow only out of the front compartment through the vent passage; and
   a first air-flow actuated noise-generating means in the vent passage for generating an audible sound when air blown into the front compartment exits through the vent passage; and
   a second air-flow actuated noise-generating means in the aperture.

2. The aerosol holding chamber defined in claim 1 wherein the means is formed with flow passage and has a tongue-like reed projecting into the passage.

3. The aerosol holding chamber defined in claim 1 wherein the partition is formed with at least one through going hole, the chamber comprising
   a valve disk having a flap overlying the hole in the partition and forming the first check valve.

4. The aerosol holding chamber defined in claim 3 wherein the body has an annular surface and the valve disk has a rim engageable with the annular surface and forming the second check valve.

5. The aerosol holding chamber defined in claim 4 wherein the body is formed adjacent the surface with a plurality of inwardly open notches.

\* \* \* \* \*